United States Patent [19]

Rothfuss et al.

[11] Patent Number: 4,534,351
[45] Date of Patent: Aug. 13, 1985

[54] LIGATOR

[75] Inventors: Robert G. Rothfuss, Bellevue, Ky.; David K. Kuhl, Cincinnati, Ohio; Federico Bilotti, Madeira, Ohio; Hugh Melling, West Chester, Ohio; Earl J. Mills, Cincinnati, Ohio

[73] Assignee: Senmed, Inc., Cincinnati, Ohio

[21] Appl. No.: 435,380

[22] Filed: Oct. 20, 1982

[51] Int. Cl.³ .................... A61B 17/04; B31B 1/00
[52] U.S. Cl. ............................ 128/334 R; 128/325; 227/19; 227/DIG. 1
[58] Field of Search ............... 128/325, 326, 346, 321, 128/334 R; 227/19, 43, 119, 132, 149, DIG. 1

[56] References Cited

U.S. PATENT DOCUMENTS

| | | | |
|---|---|---|---|
| 3,082,426 | 3/1963 | Miles | 128/325 |
| 3,270,745 | 9/1966 | Wood | 128/325 |
| 3,463,156 | 8/1969 | McDermott | 128/325 |
| 4,152,920 | 5/1979 | Green | 128/325 |
| 4,166,466 | 9/1979 | Jarvik | 128/325 |
| 4,299,224 | 11/1981 | Noiles | 128/325 |
| 4,316,468 | 2/1982 | Klieman et al. | 128/325 |
| 4,325,376 | 4/1982 | Klieman et al. | 128/325 |
| 4,430,997 | 2/1984 | DiGiovanni et al. | 128/325 |

Primary Examiner—Gene Mancene
Assistant Examiner—C. W. Shedd
Attorney, Agent, or Firm—Frost & Jacobs

[57] ABSTRACT

A disposable ligator for applying clamping clips to veins, arteries and blood vessels. The ligator comprises a first handle terminating at its forward end in a first jaw and a second jaw and a second handle, both pivotally mounted on the first handle near the forward end thereof. The handles are shiftable between open and closed positions and shift the jaws between open and closed clip-clamping positions. A clip tube containing a plurality of clips and a spring biased feeder shoe to constantly urge the clips forwardly therein is mounted in the first handle. A pusher is mounted in the first handle parallel to the clip tube in a pusher track which extends to the forward ends of the jaws. The pusher is shiftable by the first and second handles between a retracted position when the handles are closed and an extended position to locate a clip in the pusher track at the forward ends of the jaws when the handles are open. The first handle provides a ramp structure leading to the pusher track at the forward end of the clip tube which is covered by the pusher when in its extended position and exposed by the pusher when in its retracted position, thus enabling the forwardmost clip to be transferred to the pusher track in front of the pusher due to the forward urging of the clips in the clip tube, and without the necessity of moving transfer parts.

30 Claims, 14 Drawing Figures

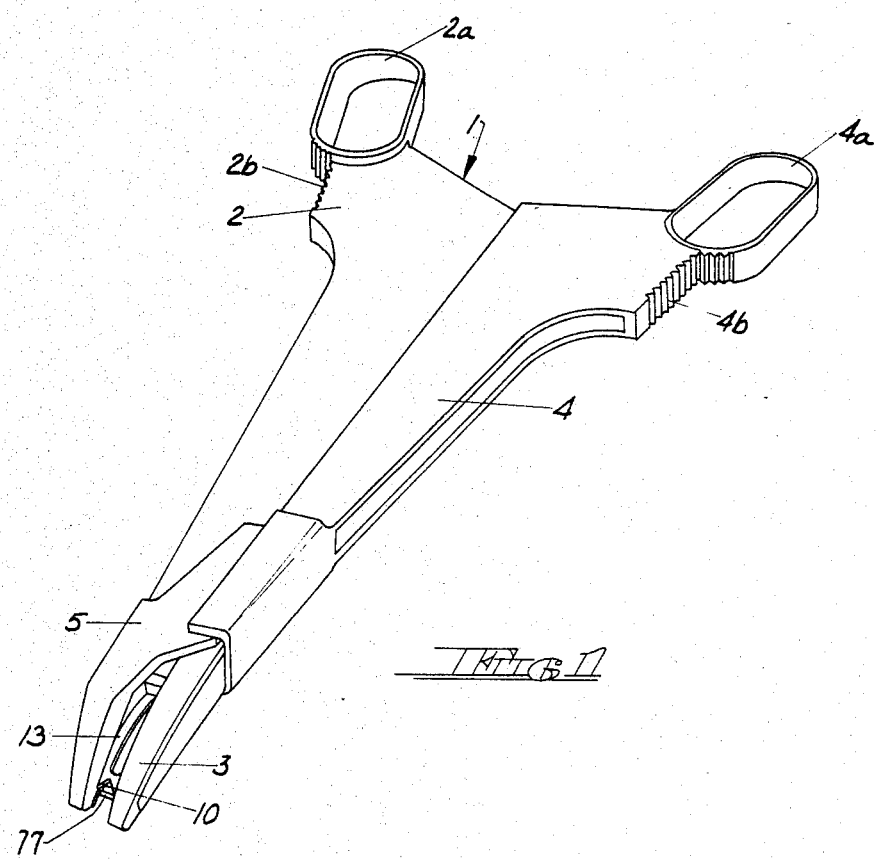

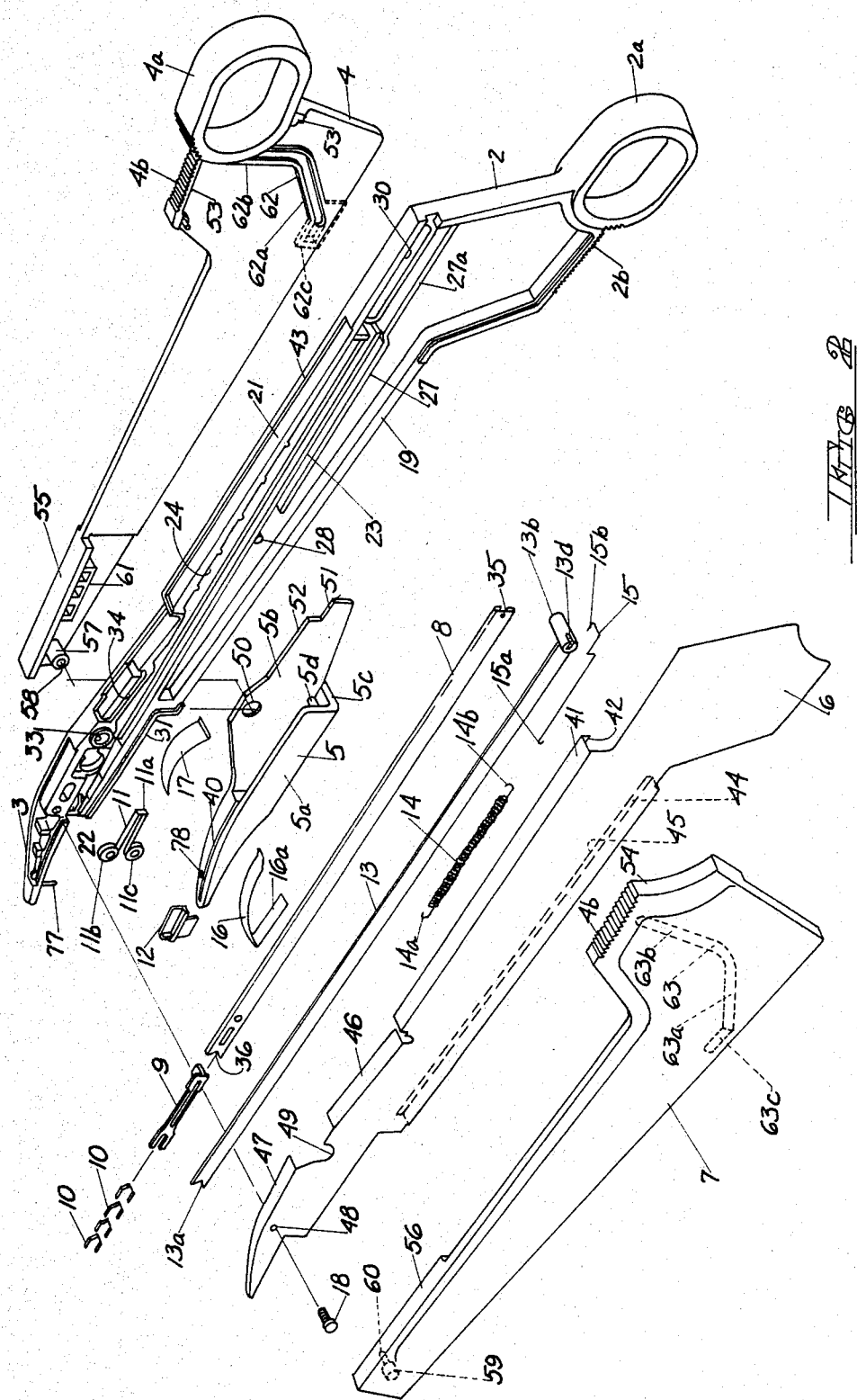

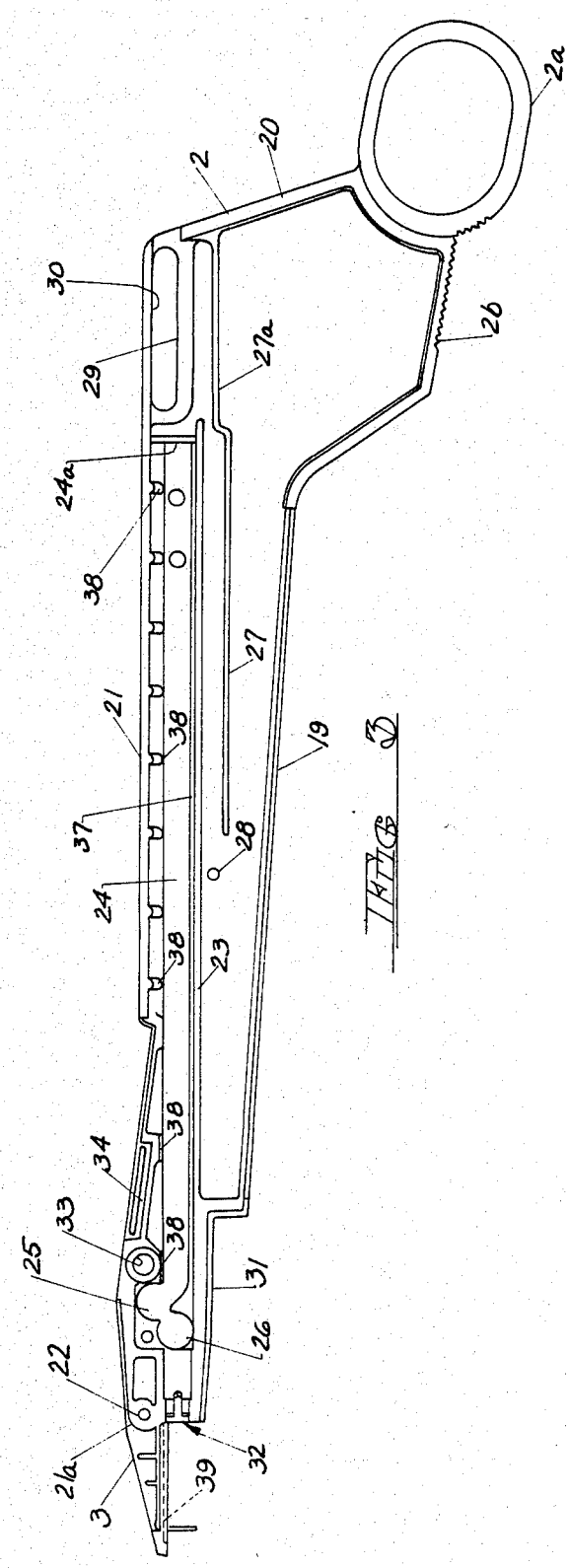

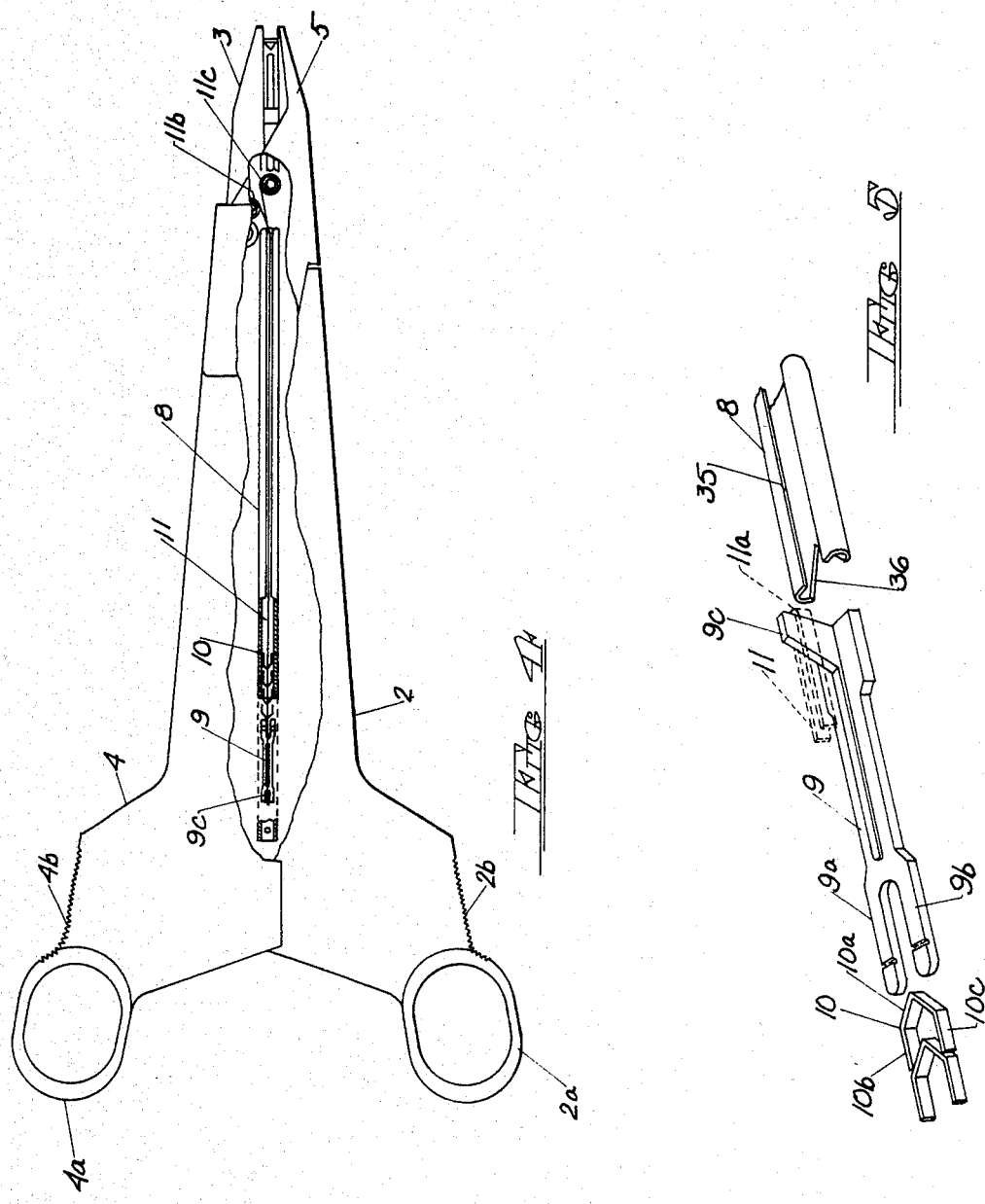

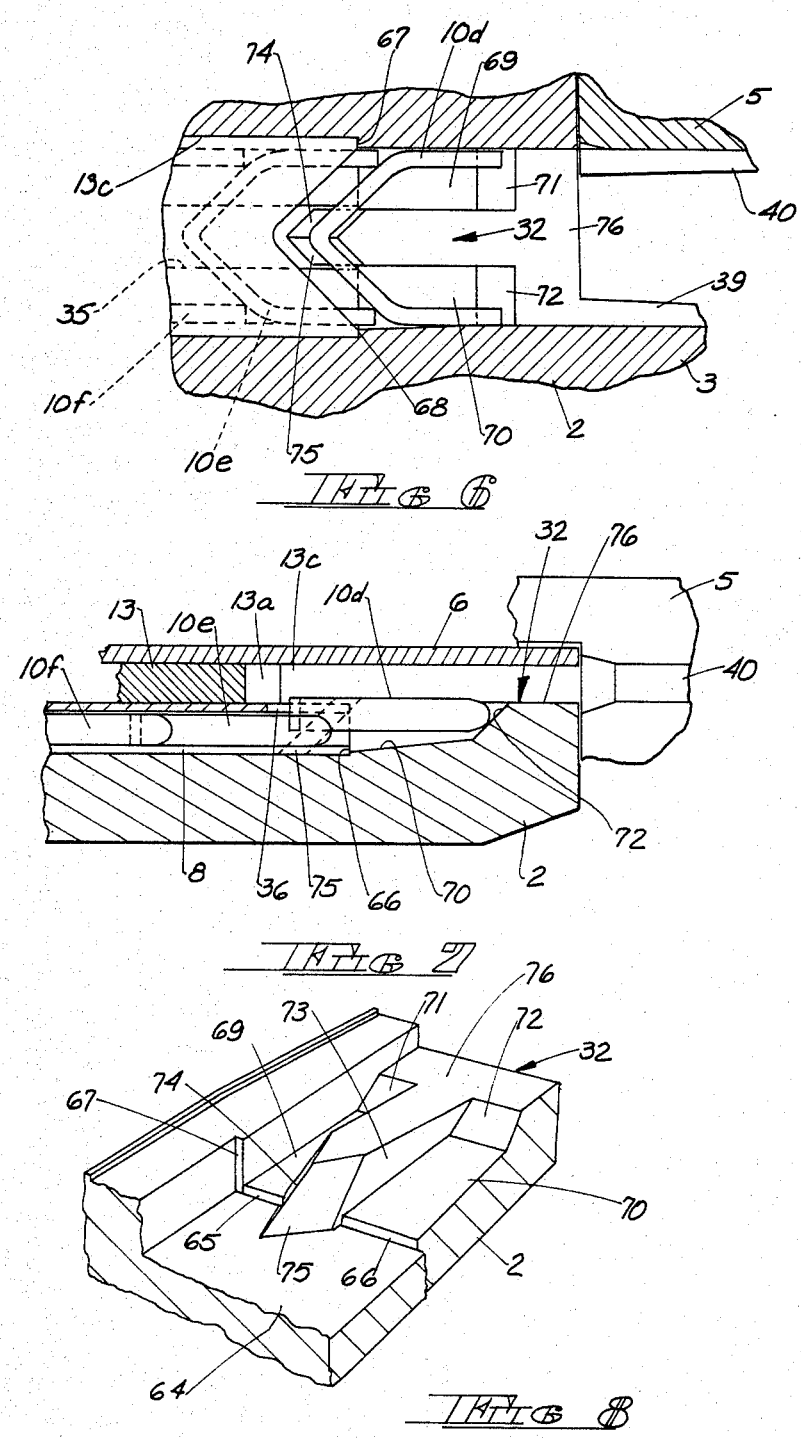

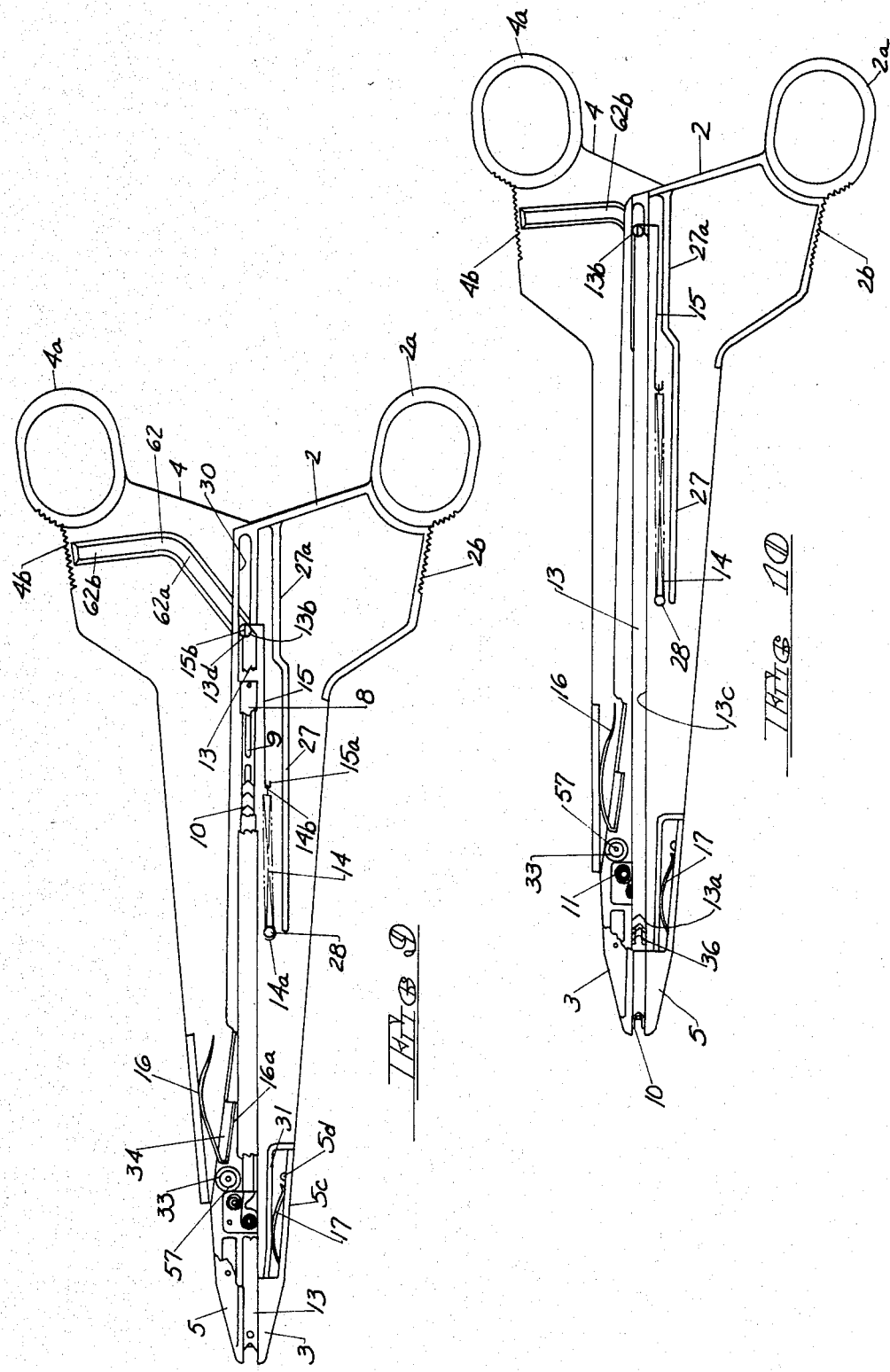

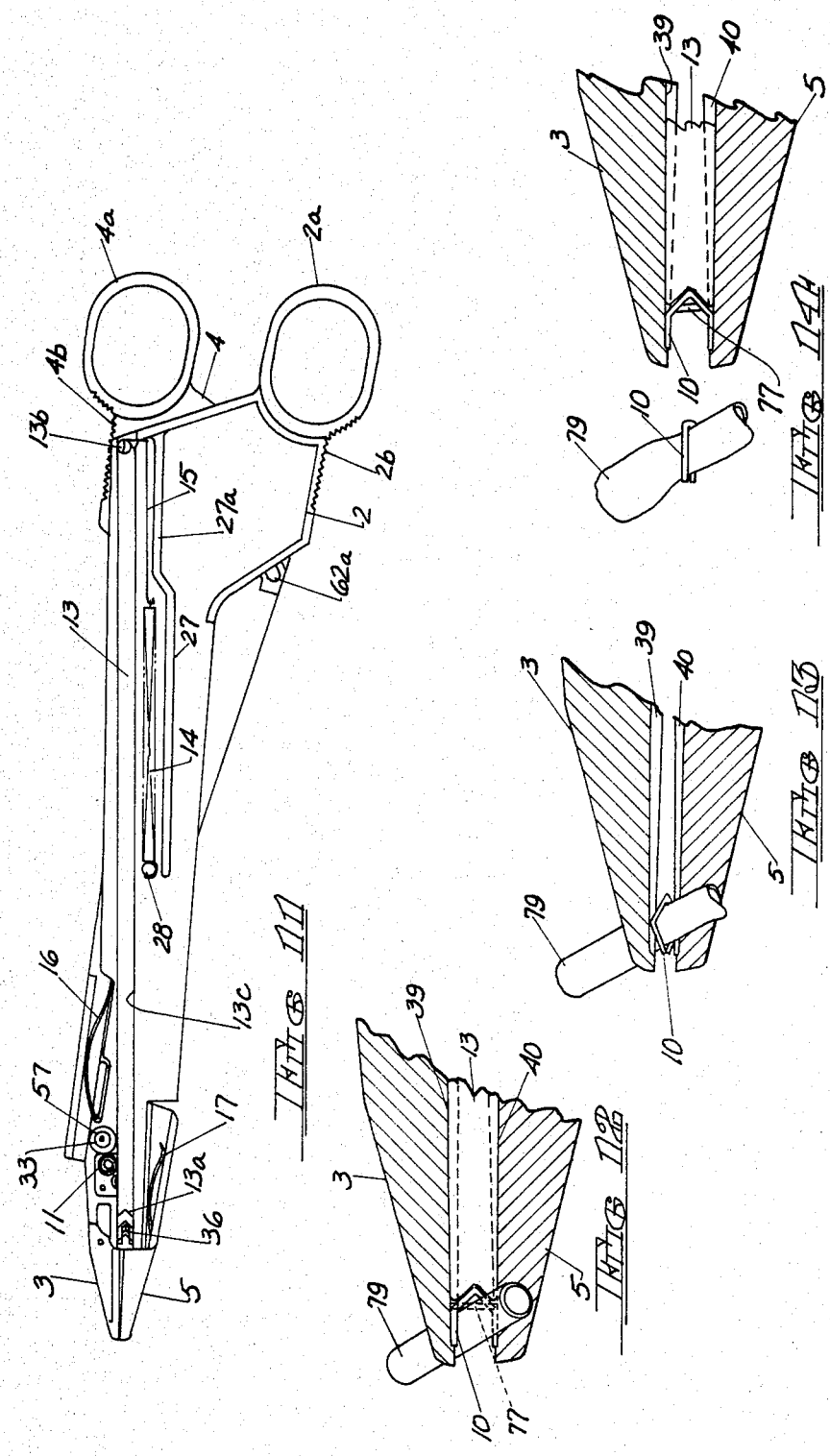

LIGATOR

TECHNICAL FIELD

The invention relates to a surgical ligator for applying clamping clips to veins, arteries, blood vessels and other body tissues, and more particularly to such a ligator characterized by smooth, easy operation, requiring less force on the part of the surgeon, and provided with an extremely reliable, substantially jam-proof clip feed system.

BACKGROUND ART

Recently there has been an increasing number of surgeons using clips, in lieu of conventional suture ties, to occlude blood vessels and the like. In a typical surgical procedure, many veins, arteries and blood vessels must be tied off, prior to the severing thereof, in order to reach the surgical site. This is an often difficult and time-consuming procedure, since many vessels are located in areas where there is little room to work. It is important that the occlusion be positive to minimize bleeding and, due to the fact that once severed, the blood-carrying vessels tend to retract into surrounding tissue and are difficult to retrieve.

Prior art workers have devised numerous types of surgical ligating instruments designed to clip blood vessels. As used herein and in the claims, the term "blood vessel" or "blood vessels" should be considered in the broad sense to be inclusive of veins, arteries and the like to which ligator clips are normally applied. Prior art ligators can be divided into a number of general groups or categories.

First of all, reusable, permanent-type ligators have been developed which resemble a hemostat. Such ligators are provided with jaws configured to accept, remove and hold a single "V"-shaped or "U"-shaped clip from a fully separate dispensing cartridge. U.S. Pat. Nos. 3,631,707 and 4,187,712 teach exemplary hemostatic clip applicators falling within this general category. Such instruments are characterized by certain drawbacks. For example, they require constant maintenance and must be cleaned after each procedure and sterilized prior to each procedure. Such instruments are normally expensive and delicate. When such instruments are employed, normally two or more of them are used so that the nurse can be loading one while the surgeon is using another. The surgeon must refocus his eyes on the vessel at the ligation site each time he changes instruments. Furthermore, a clip can easily fall out of the instrument jaws, if the nurse or surgeon depresses the handle slightly and then relaxes prior to clipping. In many such instruments, it is often possible to form clips too tightly.

A second ligator category is comprised of ligating instruments which are permanent, reusable instruments resembling a pistol. Such instruments accept pre-sterile cartridges holding a multiplicity of clips. The clips are sequentially fed as the foremost clip is formed to occlude a vessel. This type of instrument eliminates some of the shortcomings of the single-clip devices described above, but creates some new problems of its own. For example, such ligators are extremely expensive and are complex, heavy and bulky. The instrument must be disassembled and cleaned after each use and sterilized prior to each use and, therefore, requires constant maintenance. Again, it may be possible to form clips too tightly. Exemplary ligators falling within this second category are taught in U.S. Pat. Nos. 2,968,041 and 4,246,903.

The third general category relates to ligators which are intended to be disposable, single-use, multi-feed instruments. As an example, disposable instruments have been made in accordance with the teachings of U.S. Pat. No. 4,299,224 and European published application No. 0,000,875. Such devices are also characterized by certain inherent problems. The clip load is limited and the clip feed mechanism is complex and somewhat awkward. In some instances, the handles of the ligator must be spread away from each other to locate a clip in the instrument jaws, after which the handles must then be squeezed toward each other to clamp the forwardmost clip. In other instances, the clip feed mechanism requires external manual manipulation between each clip-clamping step. As a result, such instruments frequently must be removed from certain limited surgical sites to accomplish the necessary clip advance manipulations, and in some instances it is possible to form the clips too loosely.

The instrument of the present invention overcomes all of the above noted shortcomings. The instrument is capable of pre-sterilization and constitutes a disposable, single-use instrument. It is provided with an extremely simple and reliable, substantially jam-proof, automatic clip feed system which requires no force or extra manipulation on the part of the surgeon. The instrument clamps a clip and presents the next clip for use in a single hand motion.

The ligator of the present invention is lightweight, provides maximum visibility of the clip during use and has an integral stop pin to prevent the tissue and clip from sliding rearwardly of the instrument jaw tips, enabling capture of the maximum amount of tissue. An adequate consistent and repeatable force is exerted on each clip during the clip clamping procedure so that the clamped clip provides maximum security without damage to the vessel caused by excessive pressure. The instant ligator has a large clip capacity and can be made in various sizes. It can be used with equal facility by both left-handed and right-handed surgeons. A clip can be partially formed without interrupting the feeding sequence of the next clip. Finally, an automatic lockout feature can be provided to make the instrument inoperable when empty.

The reliability of the clip feed system is of utmost importance. In instruments of the type utilizing a replaceable clip cartridge, when a jam occurs the cartridge and those clips remaining therein must be removed and replaced by a new cartridge. In those disposable instruments wherein the clip magazine constitutes a permanent non-removable part of the instrument, the entire instrument must be discarded and replaced when a jam occurs.

Prior art workers have devised many types of ligator clip feeding systems. For example, U.S. Pat. Nos. 4,166,466 and 4,316,468 teach ligator instruments utilizing clip magazines or cartridges containing stacks of clips. The lowermost clip of the stack is stripped therefrom by a pusher element during the clip-applying process. Magazines of this sort are limited with respect to their clip capacity and, since they extend laterally of the instrument, they tend to limit visibility and add to the bulk of the instrument.

U.S. Pat. No. 4,316,468 also teaches a magazine wherein the clips lie in the same plane and are located one behind the other. The clips are mechanically advanced in the magazine through the interaction of a series of leaf springs extending inwardly from the housing of the magazine and a series of leaf springs coupled to a clip loading blade. The clip loading blade is actuated by a lost motion link. The above mentioned European published application No. 875 teaches a magazine again having the clips lying one behind the other in the same plane. In this instance, the clips are mechanically advanced by means of the cooperating action of a feed blade and a ratchet blade. U.S. Pat. No. 4,296,751 teaches a clip advance system wherein the clips lie one behind the other in the same plane within a magazine and are constantly urged forwardly by a spring biased follower. Once the forwardmost clip of the row is located between the forming jaws of the instrument, the remainder of the clips of the row are retracted against the urging of the follower, to permit clearance for the instrument jaws to close and clamp the forwardmost clip. All of these exemplary systems are relatively complex, most of them requiring the interaction of numerous elements.

As indicated above, the ligator of the present invention provides an extremely simple clip feed system which is essentially jam-proof and extremely reliable. The clips, lying one behind the other in the same plane, are located in a clip tube and are constantly urged forwardly by a spring biased feeder shoe. The forwardmost clip of the row is transferred to a parallel pusher track by a simple ramp structure requiring no moving parts. The pusher, slidably mounted in the pusher track, locates the clips one-by-one in their proper position between the instrument jaws for clamping. Entrance of each clip from the clip tube into the pusher track is properly timed because it is controlled by the pusher itself, as will be described hereinafter.

DISCLOSURE OF THE INVENTION

According to the invention, there is provided a disposable ligator for applying clamping clips to veins, arteries, blood vessels and other appropriate tissue. The ligator comprises a first handle terminating at its forward end in a first jaw. A second jaw is pivotally mounted to the first handle so as to cooperate with the first jaw. A second handle is pivotally mounted at its forward end to the first handle and is provided with a lug to actuate the second jaw.

The handles are shiftable between open and closed positions, and shift the first and second jaws between open and closed clip-clamping positions.

A clip tube containing a plurality of clips, lying one behind the other in the same plane, is mounted in the first handle. A feeder shoe is mounted in the clip tube and constantly urges the row of clips forwardly therein through the agency of a constant-force coil spring. Adjacent and along the clip tube, a pusher is mounted in the first handle in a pusher track which is continued to the forward ends of the jaws. The pusher is shiftable by the first and second handles between a retracted position when the handles are closed and an extended position to locate a clip in the pusher track between the forward ends of the jaws when the handles are open. The first handle provides a ramp structure leading to the pusher track at the forward end of the clip tube. The ramp structure is covered by the pusher when in its extended position. The ramp is exposed by the pusher when in its retracted position, enabling the forwardmost clip of the row to be transferred from the clip tube, via the ramp, to the pusher track in front of the pusher, due to the forward urging of the clips by the feeder shoe.

When the first and second handles are shifted from their closed to their open positions, the first and second jaws will also shift from their closed to their open positions and the pusher will locate a clip in the pusher track to a position between the forward ends of the jaws, ready for clamping. When the first and second handles are squeezed toward each other, the pusher will shift to its retracted position enabling the next forwardmost clip of the row to be ramped into the pusher track. Immediately thereafter, the first and second jaws will close, clamping the clip therebetween about the vessel to be occluded. This sequence of events is repeated with each opening and closing of the handles, the clip feeding system requiring no force on the part of the surgeon to accomplish its purpose. The first jaw may be provided with an integral stop pin which will prevent a vessel and a clip located between the jaw tips from being shoved rearwardly of the jaw tips.

BRIEF DESCRIPTION OF THE DRAWINGS

FIG. 1 is a perspective view of the ligator of the present invention illustrating the handles and jaws in their normal, open position.

FIG. 2 is an exploded perspective view of the ligator of FIG. 1, illustrating all of its parts.

FIG. 3 is a plan view of the first handle without its cover.

FIG. 4 is a plan view of the instrument, partly in cross section, illustrating the clip tube, the feeder shoe and the constant-force coil spring.

FIG. 5 is a fragmentary, exploded, perspective view illustrating the clip tube, the feeder shoe, the constant-force coil spring and several clips.

FIG. 6 is a fragmentary plan view, partly in cross section, illustrating the clip ramp of the first handle.

FIG. 7 is a fragmentary, cross sectional, elevational view of the ramp structure of FIG. 6.

FIG. 8 is a fragmentary perspective view of the ramp structure of FIGS. 6 and 7.

FIG. 9 is a simplified, semi-diagrammatic plan view of the ligator of the present invention with its handles and jaws in their normal open position.

FIG. 10 is a simplified, semi-diagrammatic plan view illustrating the instrument of FIG. 9 with its handles in their one-quarter closed position.

FIG. 11 is a simplified, semi-diagrammatic plan view of the instrument of FIG. 9 with its handles and jaws in their fully-closed position.

FIGS. 12–14 are fragmentary perspective views illustrating the application and clamping of a clip on a vessel.

DETAILED DESCRIPTION OF THE INVENTION

Reference is first made to FIG. 1 which illustrates the ligator of the present invention with its handles and jaws in normal open positions. The ligator is generally indicated at 1, having a first handle 2, terminating in a first jaw 3 at its forward end. The ligator has a second handle 4 and a second jaw 5. As will be described hereinafter, the jaw 5 and the forward end of second handle 4 are pivotally attached to the first handle 2 in such a way that second jaw 5 is actuated by second handle 4. It will be noted that handle 2 is provided with a finger loop 2a and handle 4 is similarly provided with a finger loop 4a. The edge of handle 2 adjacent to finger loop 2a is provided with a serrated gripping surface 2b which extends partway onto finger loop 2a. In an identical fashion, the handle 4 is provided with a gripping surface 4b along its edge adjacent to finger loop 4a and extending partway onto finger loop 4a.

Reference is now made to FIG. 2. This Figure is an exploded view of the ligator of FIG. 1, illustrating all of its parts. To this end, first handle 2 is shown terminating in first jaw 3. Second handle 4 is also shown, together with second jaw 5.

First handle 2 is completed by a cover member 6. Similarly, second handle 4 is completed by a cover member 7. The ligator is provided with a magazine or clip tube 8, a clip feeder shoe 9, a plurality of clips, four of which are shown at 10, a constant-force coil spring 11 and a cover 12 for the constant-force coil spring. The ligator further comprises a pusher 13, a pusher coil spring 14 and a wire link 15. To complete the structure, there is a handle biasing spring 16, a jaw biasing spring 17 and a cover screw 18. All of these elements will be described in detail hereinafter.

While the ligator of the present invention could be manufactured as a permanent, reusable surgical instrument, it lends itself well to being produced as a disposable, single-use instrument. To this end, all of the parts of the instrument may be readily molded of plastic with the exception of cover 6, clip tube 8, springs 11, 14, 16 and 17, wire link 15 and screw 18. These last mentioned elements are preferably made of metal. Jaw 5 is preferably made of a filled plastic for additional strength. The plastic and metallic materials from which the elements are made must be chosen from those well known groups thereof which are compatible with a surgical environment and are capable of being sterilized by autoclave, ethylene oxide, irradiation, or other standard methods.

Reference is now made to FIG. 3 which illustrates, in the form of a plan view, the inside surface of first handle 2. The handle 2 constitutes an elongated, integral, one-piece molded member. At its rearward end, the handle terminates in finger loop 2a. At its forward end, it terminates in first jaw 3. Handle 2 is substantially surrounded by peripheral wall portions 19, 20 and 21. The wall 21 extends to the first jaw 3 and terminates in a rounded end 21a containing a bore 22 adapted to receive first handle cover screw 18 (see FIG. 2), as will be described hereinafter.

An internal longitudinal wall 23 lies in parallel spaced relationship to the majority of wall 21, and together they define a longitudinal channel 24. The channel 24 extends from the front end of handle 2, terminating at 24a. Near its forward end, the channel 24 contains a pair of sockets 25 and 26.

Handle 2 is provided with a second longitudinally extending internal wall 27, which cooperates with the wall 23 to confine pusher coil spring 14 (see FIG. 2), as will be described hereinafter. An integral post 28 serves as a mount for one end of the pusher coil spring 14. A slightly inset continuation 27a of wall 27 cooperates with an adjacent internal wall 29 to confine the wire link 15, again as will be described hereinafter. Between peripheral wall 21 and internal wall 29, the handle 2 is provided with an elongated opening or slot 30, the purpose of which will be clear hereinafter.

The forward end of handle 2 is notched as at 31 and is provided with a ramp structure generally indicated at 32 in channel 24. The notch 31 and ramp structure 32 will be fully described hereinafter. To complete handle 2, a pivot bore 33 is provided to receive pivot means by which the second jaw 5 and second handle 4 are pivotally affixed to handle 2. An elongated channel or slot 34 is also formed in handle 2 to receive the base portion 16a of handle biasing spring 16 (see FIG. 2) by which the handles are biased to their open position, as will be described hereinafter.

Reference is now made to FIGS. 2 and 5. As is clear from these Figures, the clip tube 8 comprises a metallic member of C-shaped cross section, the longitudinal edges of the clip tube 8 defining an elongated longitudinal slot 35 extending the length of the clip tube.

While the ligator clips may be of any appropriate and well known configuration, they are each illustrated as comprising a V-shaped crown 10a, terminating in forwardly extending legs 10b and 10c. The forward end of the clip tube 8 is notched as at 36 so as to conform to the shape of the crown 10a of the ligator clips.

Feeder shoe 9 comprises an elongated plastic member of such dimensions that it will be received within clip tube 8 with a sliding fit. At its forward end, the feeder shoe 9 is provided with bifurcations 9a and 9b adapted to abut either side of the crown portion 10a of the rearwardmost ligator clip of the row. At its rearward end, the feeder shoe has an upstanding lug 9c so dimensioned as to extend through clip tube slot 35 with a sliding fit.

The constant-force spring 11 (see FIG. 2) constitutes a ribbon-like spring formed into a U-shape having a base 11a and leg portions terminating in coils 11b and 11c. The spring 11 is of the well-known type which exerts a substantially constant force regardless of the amount by which it is extended. Such springs are sold under the tradename "Neg-A-Tor". As is suggested in FIG. 5, the base 11a of spring 11 is adapted to be engaged about the upstanding lug 9c of feeder shoe 9.

Returning to FIG. 3, it will be noted that handle 2 is provided with a ledge or shelf-like structure 37 extending along internal upstanding wall 23 within the channel 24. Ledge 37 also surrounds sockets 25 and 26. On the other side of elongated channel 24, peripheral wall portion 21 is provided with a plurality of inwardly extending lugs 38. The upper surface of these lugs 38 and the upper surface of ledge 37 (as viewed in FIG. 3) are coplanar and are spaced upwardly from the bottom of channel 24. The lugs 38 and ledge 37 are adapted to receive and support clip tube 8, with slot 35 of clip tube 8 facing toward the bottom of the channel 24 of handle 2. It will be understood that when the clip tube 8 is mounted in handle 2, its forward end (containing notch 36) will lie adjacent to the ramp structure 32 (see FIG. 3).

FIG. 4 is a plan view of the ligator instrument of FIG. 1, illustrating the opposite side of first handle 2 from that shown in FIG. 3. First handle 2, second handle 4 and second jaw 5 are partially broken away to illustrate clip tube 8 mounted in place within handle 2. It will be understood by one skilled in the art that clip tube 8 will contain a row of ligator clips 10 and feeder shoe 9. When the feeder shoe 9 is located within clip tube 8 and clip tube 8 is mounted in first handle 2, the upstanding lug 9c of feeder shoe 9 will extend into the elongated channel 24 of handle 2. The constant-force coil spring 11 will be mounted within the elongated channel 24 with its base portion 11a extending about the feeder shoe lug 9c and its coil portions 11b and 11c located respectively in sockets 25 and 26, as suggested by FIG. 4. Coil portions 11b and 11c will be maintained in sockets 25 and 26 by cover 12 (see FIG. 2). As a result of this structure, the clip tube 8 serves as a magazine for the ligator clips 10 and the ligator clips 10 are constantly urged forwardly (i.e. toward the instrument jaws) within clip tube 8 by the action of constant-force spring 11 on feeder shoe 9.

Returning to FIG. 2, the pusher 13 comprises an elongated, flexible plastic member having a notch 13a at its forward end. The notch 13a corresponds to the V-shaped crown 10a of each ligator clip 10. At its rearward end, the pusher 13 is provided with an integral, transversely extending, cylindrical lug 13b. At one end, the lug 13b has a small slot 13d formed therein, the purpose of which will be apparent hereinafter.

The pusher 13 is adapted to overlie clip tube 8 within the channel 24 of handle 2. The cylindrical lug 13b of pusher 13 extends through the elongated slot 30 of handle 2 (see FIG. 3). The walls 21 and 23 of handle 2 cooperate with the clip tube 8 to form a pusher track 13c for pusher 13.

As is most clearly seen in FIGS. 1 and 2, the first jaw 3 and the second jaw 5 are slightly curved, as is typical of many ligators, to facilitate the instrument's use and increase visibility of the clip during the clip clamping procedure. As is shown in FIG. 3, first jaw 3 has a groove 39 formed therein and extending nearly to the end of the jaw. FIG. 2 illustrates a corresponding groove 40 in second jaw 5. The grooves 39 and 40 constitute continuations of the pusher track 13c. As a result, the pusher is always captive within the instrument throughout its path of travel.

Pusher 13 is shiftable within the pusher track 13c between a retracted position and an extended position. The retracted position of the pusher is illustrated in FIG. 11. It will be noted that the forward end 13a of pusher 13, when the pusher is in its retracted position, lies just behind the notched forward end 36 of clip tube 8. The forwardmost position of pusher 13 is illustrated in FIG. 9. In its forwardmost position, the notched front end 13a of the pusher is located near the forward ends of jaw grooves 39 and 40 so that it can locate a ligator clip 10 at the forwardmost ends of these grooves. The means by which the pusher 13 is shifted between its retracted and extended positions will be described hereinafter.

Returning to FIG. 2, pusher spring 14, constituting a coil spring, has a hook-shaped configuration 14a at its forward end and a similar hook-like configuration 14b at its rearward end. Wire link 15 has a hook-shaped forward end 15a and a short forwardly extending portion 15b at its rearward end. As is most clearly shown in FIG. 9, the forward end 14a of spring 14 is mounted on post 28 of handle 2. The rearward end 14b of spring 14 is engaged by the hook-shaped forward end 15a of wire link 15. The forwardly extending rearward end 15b of wire link 15 is located in the slot 13d of lug 13b at the rearward end of pusher 13. As a consequence of this, the coil spring 14 constantly urges pusher 13 forwardly, for reasons which will be apparent hereinafter.

Attention is now directed to FIGS. 2, 3 and 9. Handle biasing spring 16 is in the form of a leaf spring, having a base portion 16a. The base portion 16a is located in the slot 34 formed in handle 2. The remainder of handle biasing spring 16 is adapted to abut second handle 4 and its cover 7 to urge the second handle to its openmost position, as illustrated in FIG. 9.

With the constant-force spring 11 and its cover 12, the clip tube 8 and its feeder shoe 9 and row of ligator clips 10, pusher 13 and its spring 14 and wire link 15, and handle biasing spring 16 all mounted within handle 2, the first handle cover 6 may be applied to handle 2 to complete this structure and to maintain all of the above mentioned elements in place therein. As is clearly shown in FIG. 2, the first handle cover member 6 has a flange 41 with an inturned edge 42. The flange 41 is adapted to overlie a part of handle 2 peripheral wall 21. The peripheral wall 21 is provided with a narrow slot 43. The inturned edge 42 of flange 41 is adapted to engage slot 43 with a snap fit.

The cover member 6 has a second flange 44 with an inturned edge 45. The flange 44 is adapted to overlie a part of the peripheral wall 19 of handle 2. Peripheral wall 19 is provided with a longitudinal slot (not shown) similar to slot 43 of peripheral wall 21 and adapted to be engaged by the inturned edge 45 of flange 44 with a snap fit. Cover 6 has a third flange 46. This flange overlies the peripheral portion of handle 2 containing the slot 34 in which the base 16a of handle biasing spring 16 is mounted. As a result, the base 16a of handle biasing spring 16 is captively mounted within first handle 2. Finally, the cover 6 is provided with a fourth flange 47 adapted to enclose the forwardmost part of handle 2 and the upper part of first jaw 3. It will be understood that the forward end of cover 6 and flange 47 will be appropriately curved to match the curve of first jaw 3. To assure that the cover fits snuggly against first handle 2 at the jaw area thereof, the cover is provided with a perforation 48 through which screw 18 extends and is threadedly engaged in the bore 22 of first handle 2 (see FIG. 3). Finally, cover 6 is provided with a notch 49. The notch 49 is present to expose pivot bore 33 in first handle 2.

As is most clearly shown in FIG. 2, the molded plastic jaw 5 comprises a solid forward jaw portion containing the pusher track groove 40. The rearward portion of the jaw is hollow, comprising a side wall 5a, a side wall 5b, a bottom wall 5c and a low end wall 5d. These walls define a chamber adapted to receive jaw biasing spring 17 (see also FIG. 9).

Second jaw 5 is mounted on first handle 2 with the forward portion of first handle 2 received between second jaw walls 5a and 5b and the forward portion of second jaw 5 adjacent to first jaw 3. The wall 5b of second jaw 5 has a perforation 50 formed therein, adapted to be located coaxially with pivot bore 33 of first handle 2. It will be noted from FIG. 9 that when the second jaw 5 is in position on first handle 2, the notched portion 31 of first handle 2 closes the chamber formed by the walls 5a through 5d of second jaw 5. The jaw biasing spring 17 acts upon the surface of notch 31 of first handle 2 and the wall 5c of second jaw 5 to urge the second jaw 5 to its open position as illustrated in FIG. 9.

Returning to FIG. 2, the wall 5b of second jaw 5 has a notch 51 formed therein. This notch cooperates with an integral lug (not shown) on first handle 2 to determine the openmost position of second jaw 5. The wall 5b of second jaw 5 also has a cam surface 52 thereon, the purpose of which will be evident hereinafter.

With second jaw 5 and its associated jaw biasing spring 17 mounted on first handle 2, the ligator 1 may now be completed by the addition of second handle 4 and its cover 7. Second handle 4 has a transversely extending flange 53 containing a portion of finger grip 4b and extending about the forward end of finger loop 4a, as shown in FIG. 2. The second handle cover 7 has a complimentary transversely extending flange 54, also containing a portion of finger grip 4b. At its forward end, second handle 4 has a second transversely extending flange 55. Second handle cover 7 has a corresponding flange 56. The mating edges of second handle flange 53 and second handle cover flange 54 are intended to be joined together by any appropriate means such as gluing, welding or the like. The same is true of the mating edges of second handle flange 55 and second handle cover flange 56. By virtue of this joinder, second handle 4 and its cover 7 are spaced from each other by a distance sufficient to just nicely receive the first handle 2 and its associated parts.

The second handle 4, at its forward end, has a laterally extending, cylindrical lug 57 with a bore 58 therein. At a corresponding position, second handle cover 7 has a cylindrical lug 59 terminating in a pin 60. Lugs 57 and 59 are intended to be joined together, with the pin 60 extending into the bore 58. Cylindrical lugs 57 and 59 extend through the perforation 50 in the wall 5b of first jaw 5 and the pivot bore 33 of second handle 2, thereby serving as a pivot pin for handles 2 and 4, and second jaw 5.

Second handle 4, near its forward end, has a lug 61. The lug 61 is so positioned as to contact the cam surface 52 of second jaw 5 to close the jaw, when first handle 2 and second handle 4 are closed.

The second handle 4, as shown in FIG. 2, is provided with an L-shaped groove 62 on its inside surface, near its rearward end. The L-shaped groove 62 has a first leg 62a and a second leg 62b. As shown in broken lines in FIG. 2, the second handle cover 7 has a corresponding L-shaped groove 63 with legs 63a and 63b. The grooves 62 and 63 are mirror images of each other.

Reference is now made to FIG. 9. FIG. 9, being a somewhat simplified drawing, illustrates first handle 2 without its cover 6 and second handle 4, without its cover 7. In addition, second jaw 5 is partially broken away. It will be noted that the transverse cylindrical lug 13b of pusher 13 extends downwardly through rectilinear slot 30 of first handle 2 and is engaged in the groove 62 of second handle 4. It will be understood that the other end of transverse cylindrical lug 13b will similarly be located in the groove 63 of second handle cover 7, occupying the same relative position therein.

In FIG. 9, first handle 2 and second handle 4 are shown in their open positions, as determined by the transverse cylindrical lug 13b of pusher 13 being located at the free end of second handle groove leg 62a. When first handle 2 and second handle 4 are squeezed together, the slot 30 of first handle 2 and the groove leg 62a of second handle 4 will cooperate to shift transverse pusher lug 13b rearwardly, thus shifting pusher 13 toward its retracted position. When the handles 2 and 4 have moved together so as to be about one quarter closed (as shown in FIG. 10), the transverse pusher lug 13b will have nearly reached the juncture of second handle groove legs 62a and 62b. As a result of this, the forward end 13a of pusher 13 will have been removed from between jaws 3 and 5 and pusher 13 will have nearly reached its fully retracted position wherein the forward end 13a of pusher 13 is located just behind the forward or notched end 36 of clip tube 8. It is at this point that the lug 61 of second handle 4 contacts the cam surface 52 of second jaw 5 to begin to close the jaw toward first jaw 3 (see also FIG. 2).

FIG. 11 illustrates first handle 2 and second handle 4 in their fully closed position. Once the transverse pusher lug 13b has entered second handle groove leg 62b, it will be maintained in its retracted position, but will not shift further toward the rear of the instrument. With the handles 2 and 4 in their closed position, the transverse cylindrical pusher lug 13b approaches the free end of second handle groove leg 62b.

As first handle 2 and second handle 4 are shifted toward their open positions, the transverse pusher lug 13b will initially ride along leg 62b of the second handle groove 62 with no forward motion of pusher 13. In the meantime, however, jaws 3 and 5 will have opened, as shown in FIG. 10. As first handle 2 and second handle 4 are shifted the rest of the way toward their open positions, the transverse pusher lug 13b will enter and ride along second handle groove leg 62a, causing the pusher 13 to enter the jaws 3 and 5 and to achieve its extended position, as shown in FIG. 9. It will be understood that the cylindrical lug 13b of pusher 13 cooperates with second handle cover groove 63 in the same manner as it does with second handle groove 62.

From the description thus far, it will be apparent that in order for pusher 13 to locate a ligator clip at the forwardmost ends of jaws 3 and 5, it is necessary to cause each of the clips in the clip tube 8 to shift, in its turn, from the clip tube 8 into the pusher track 13c so that it can be engaged by the notched forward end 13a of pusher 13. To cause each clip 10 to shift from clip tube 8 to the pusher track, the ramp generally indicated at 32 in FIG. 3 is used. Ramp 32 constitutes an integral part of first handle 2.

Ramp 32 is best illustrated in FIGS. 6-8. Referring first to FIG. 8, just rearwardly of ramp 32, there is a surface 64. The surface 64 lies in the same plane as the ledge 37 and lugs 38 which support the clip tube 8. The surface 64 is adapted to support the forwardmost end of clip tube 8. At the forward end of surface 64, there are shoulders 65 and 66 with substantially coplanar vertical shoulders 67 and 68. The shoulders 65-68 constitute abutment surfaces for the forward end of clip tube 8 and these abutment surfaces are of a dimension slightly less than the thickness of the metal from which the clip tube 8 is made.

The ramp 32 comprises parallel spaced ramp surfaces 69 and 70 which gradually slope upwardly and forwardly. Ramp surfaces 69 and 70 terminate respectively in ramp surfaces 71 and 72 which slope forwardly and upwardly at a steeper angle. Surfaces 69 and 71 are separated from surfaces 70 and 72 by a wall or projection 73 which, at its rearward end, is V-shaped, terminating in upwardly and forwardly sloping surfaces 74 and 75. The upwardly and forwardly sloping surfaces 71 and 72 and the upwardly and forwardly sloping surfaces 74 and 75 terminate in the planar upper surface 76 of the ramp 32 which is substantially coplanar with the upper surface of clip tube 8 and constitutes a part of the pusher track 13c for pusher 13. The surfaces 69 and 71 cooperate with one leg of a forwardmost clip of the row being ramped and surfaces 70 and 72 cooperate with its other leg. The surfaces 74 and 75 cooperate with the crown portion 10a of the forwardmost clip to cause the clip to shift from clip tube 8 to the pusher track 13c while always remaining in a plane substantially parallel to that of the clip tube 8 and that of the pusher track 13c. This is demonstrated in FIGS. 6 and 7.

It will be remembered that the row of clips 10 in clip tube 8 are constantly urged forwardly by the action of feeder shoe 9 and constant-force spring 11. It will further be remembered that, when first handle 2 and second handle 4 are in their normal, open positions, the pusher 13 will be in its extended position with its forward end between jaws 3 and 5. Thus, the pusher 13, in its extended position, will overlie the upper surface 76 of ramp 32 closing the passage between clip tube 8 and the pusher track 13c. Under these circumstances, the forwardmost clip in clip tube 8 can extend partway out of the forward end of the clip tube, but as it moves along surfaces 69 and 70 and begins to rise, it will abut the pusher 13 which will prevent further forward movement of the forwardmost clip.

When the pusher 13 is in its retracted position, its notched forward end 13a will be located just behind the notched forward end 36 of clip tube 8. Thus, the pusher 13 no longer overlies the upper surface 76 of ramp 32. The forwardmost clip shown at 10d in FIGS. 6 and 7, under the urging of the next succeeding clip 10e, will travel along surfaces 69 and 70 until the forward ends of its legs engage surfaces 71 and 72 of ramp 32. At the same time, the crown portion of the forwardmost clip 10d will engage the rearward surfaces 74 and 75 of wall 73. Further forward urging of the clip 10d will cause it to rise into the pusher track 13c. The forward ends of the second clip 10e will ultimately lose contact with the crown portion of the first clip 10d and will begin to slip under the first clip 10d completing its shift into the pusher track 13c and into abutment with cover 6. When the pusher 13 is again shifted to its extended position, it will locate the forwardmost clip 10d between jaws 3 and 5 with the forward ends of the legs of clip 10d abutting the ends of jaw grooves 39 and 40, which constitute a part of the pusher track 13c. Meanwhile, the pusher 13 again overlies the upper surface 76 of ramp 32 preventing further forward movement of second clip 10e under the urging of third clip 10f. In this way, each clip in its turn is shifted from clip tube 8 to the pusher track 13c by the ramp structure 32 which operates in a simple and efficient manner with no moving parts.

The ligator 1 of the present invention, having been described in detail, its operation can be set forth as follows. The ligator will be assembled, loaded with clips, packaged and sterilized by any of the methods mentioned above.

At the time of use, the ligator will be removed from its package and handed to the surgeon with its first handle 2 and second handle 4 in their normal, open positions. The ligator may be packaged with a first clip located between jaws 3 and 5. If not, then the surgeon will have to cycle the ligator once to bring a first clip into position for clamping between jaws 3 and 5. The instrument, ready for use, is illustrated in FIGS. 1 and 9.

The surgeon locates the forwardmost clip (between jaws 3 and 5) about the vessel to be clamped and then squeezes handles 2 and 4 toward each other. As indicated above, as the handles are squeezed together about one quarter of the distance to their fully closed position (see FIG. 10), the interaction of grooves 62 and 63 of second handle 4 and its cover 7 with slot 30 of handle 2 and the transverse cylindrical lug 13b of pusher 13 will cause the pusher to shift rearwardly to its retracted position, clearing the pusher from between the jaws 3 and 5. As handles 2 and 4 are shifted to their fully closed positions (FIG. 11), lug 61 of second handle 4 contacts cam surface 52 of second jaw 5 causing the jaws 3 and 5 to close, clamping the clip about the vessel.

Meanwhile, once pusher 13 achieves its retracted position (FIG. 10), it exposes ramp 32. The row of clips within clip tube 8 is then free to move forwardly under the influence of feeder shoe 9 and constant-force spring 11. Through the agency of ramp 32, the next forwardmost clip of the row is ramped into the pusher track. Thus, the next clip of the row is located in the pusher track 13c while the surgeon is completing the clip-clamping step. This action is automatic and requires no force to be exerted by the surgeon and no additional manipulation on his part.

It will be noted from a comparison of FIGS. 10 and 11 that during the clip-clamping procedure, once the pusher 13 has achieved its retracted position, it will remain in its retracted position while the handles are completely closed, as in FIG. 11, because the cylindrical lug 13b of pusher 13 will be traveling in the legs 62b and 63b of grooves 62 and 63 of second handle 4 and its cover 7.

Once the clip-clamping procedure has been completed, the surgeon simply relaxes his grip on the ligator 1, allowing first handle 2 and second handle 4 to shift to their fully open position under the influence of handle biasing spring 16. Again looking at FIGS. 11 and 10, as the handles 2 and 4 shift from their fully closed positions (FIG. 11) to their three-quarter open positions (FIG. 10), the pusher 13 will remain in its retracted position, because the lug 13b of pusher 13 is riding in groove legs 62b and 63b of second handle 4 and its cover 7. Simultaneously, the lug 61 of second handle 4 cooperates with cam surface 52 of second jaw 5 in such a way as to permit jaw biasing spring 17 to return second jaw 5 to its open position.

When the handles reach their three-quarter open positions, as shown in FIG. 10, the transverse lug 13b of pusher 13 will enter groove legs 62a and 63a of second handle 4 and its cover 7. This will result in the shifting of the pusher 13 to its extended position as the handles 2 and 4 shift from their three-quarter open position (FIG. 10) to their fully open position (FIG. 9). As pusher 13 shifts to its extended position, it will pick up the previously ramped clip, located in the pusher track 13c, and shift it forwardly to the forwardmost ends of jaw grooves 39 and 40, in position for the next clip-clamping procedure. At this point, the cycle of the ligator 1 is complete. The cycle may be performed as many times as there are clips in clip tube 8. The clip tube 8 is capable of holding 35 or more clips. When the ligator is empty, it is simply disposed of and a new ligator is readied for use.

While not required for the operation of ligator 1, it is preferred that the first jaw 3 be provided with an integral pin. Such a pin is shown at 77 in FIG. 2. The free end of pin 77 is adapted to be received in a perforation 78 in second jaw 5 (see FIG. 2). Pin 77 is of such length that its free end extends into perforation 78 of second jaw 5, even when the jaws 3 and 5 are in their open positions. When the jaws 3 and 5 are shifted to their closed position, pin 77 is totally received within perforation 78.

Pin 77 is so positioned on jaw 3 that it lies to the side of and adjacent the apex of the crown portion of the forwardmost clip when located in its clamping position at the forward end of jaws 3 and 5. This is illustrated in FIGS. 12 and 14.

Turning to FIG. 12, this Figure illustrates a clip 10 being located about a vessel 79 to be clamped. The vessel is inserted between the legs of clip 10 and the ligating instrument 1 is shifted forwardly until vessel 79 contacts pin 77. The pin 77 precludes locating vessel 79 too deeply between jaws 3 and 5, inadvertently shoving clip 10 and pusher 13 rearwardly. Thus, pin 77 assures proper positioning of vessel 79 and assures that the clip 10 will remain in its proper position relative to jaws 3 and 5 for clamping.

During the clamping procedure, the pusher 13 shifts rearwardly and then jaws 3 and 5 begin to close. By virtue of its shape, as the clip is initially squeezed, the free ends of its legs will come together as shown in FIG. 13, assuring that the clip 10 envelops the vessel 79. Further closing of the jaws will flatten the clip 10 thoroughly clamping the vessel 79. The configuration of the ligating instrument and grooves 62 and 63 is such that too much clamping pressure cannot be applied to the clip and the clip cannot be over-clamped.

When the handles are returned to their normal open positions, the clip is released from jaws 3 and 5 and a new clip 10 is positioned for the next clamping procedure, as shown in FIG. 14.

Modifications may be made in the invention without departing from the spirit of it. For example, the ligator means may be provided with indicator means (not shown) or a window (not shown) providing the surgeon with a visual indication of the number of clips remaining in the instrument.

It is also within the scope of the invention to provide the instrument with a safety means locking first handle and second handle 4 (and thus the jaws 3 and 5) in their open positions after the last ligator clip has been clamped. This can be accomplished in a number of ways.

A very simple way is illustrated in FIG. 2.

To achieve the safety lock-out, it is only necessary to extend the free ends of groove leg 62a of second handle 4 and groove leg 63a of second handle cover 7. Such extensions are shown in broken lines at 62c and 63c in FIG. 2. The extensions 62c and 63c are so positioned as to be parallel to the slot 30 of first handle 2 when the handles are in their open positions as shown in FIG. 9. When a clip is located at the ends of jaw grooves 39 and 40 of jaws 3 and 5, such a clip will determine the extended position of pusher 13. Under these circumstances, the transverse cylindrical lug 13b of the pusher cannot enter the groove extensions 62c and 63c. However, when the last ligator clip is clamped, and the handles 2 and 4 are shifted to their normal open positions, there will be no clip at the forward ends of jaw slots 39 and 40 so that pusher 13 will shift forwardly until its forward end abuts the forward ends of jaw slots 39 and 40. This slight extra forward movement of pusher 13 is enough to cause the transverse pusher lug 13b to enter the groove extensions 62c and 63c. Since the groove extensions are parallel to the elongated slot 30 of handle 2, an attempt to squeeze handles 2 and 4 together will not cause movement of pusher 13 and the instrument will essentially be locked in its normal, unactuated, open position. With this type of safety lock-out, it will be necessary to package the ligator with a first clip located between jaws 3 and 5.

What is claimed is:

1. An instrument for applying ligating clips to blood vessels, said instrument comprising a first handle terminating at its forward end in a first jaw, a second handle and a second jaw both pivotally mounted on said first handle near said forward end thereof, said first and second handles being manually shiftable between open and closed positions, said first jaw being shiftable by said first handle and said second jaw being shiftable by said second handle between open and closed clip-clamping positions, an elongated magazine within said first handle and extending longitudinally therein, a row of clips located within said magazine together with means constantly urging said row of clips toward said forward end of said magazine, a pusher being mounted within said first handle parallel to and adjacent to said magazine in a pusher track which extends to the forward ends of said first and second jaws, said pusher being shiftable by said first and second handles between a retracted position removed from said jaws when said handles are in their closed positions and an extended clip-locating position between said jaws when said handles are in their open positions, a ramp in said first handle at the forward end of said magazine and leading to said pusher track, said ramp being covered by said pusher when in its extended position and exposed by said pusher when in its retracted position to enable the forwardmost clip of said row to be transferred from said magazine to said pusher track under the influence of said urging means.

2. The instrument claimed in claim 1 wherein said clips have a crown portion terminating in legs, said clips lying legs-foremost one behind the other in the same plane within said magazine, said ramp having first and second ramp surfaces for each clip leg to lift the legs of each clip into said pusher track, said first ramp surfaces sloping forwardly and toward said pusher track at a shallow angle and terminating in said second ramp surfaces sloping forwardly and toward said pusher track at a steeper angle terminating at said pusher track, said first and second ramp surfaces for one clip leg being separated from said first and second ramp surfaces for the other clip leg by a wall portion, said wall portion having a rearward end adjacent the forward end of said magazine, said wall portion rearward end terminating in at least one ramp surface extending forwardly and to said pusher track to lift the crown of each clip into said pusher track.

3. The instrument claimed in claim 2 wherein said ramp comprises an integral, one-piece part of said first handle.

4. The instrument claimed in claim 2 including spring means biasing said handles to their open positions.

5. The instrument claimed in claim 4 including spring means to bias said second jaw to its open position.

6. The instrument claimed in claim 5 including a rectilinear slot in said first handle located rearwardly of said pusher track and extending parallel thereto, said first handle having a cover enclosing said pusher track and exposing said slot, said second handle having a cover affixed thereto in parallel spaced relationship, said second handle cover being spaced from said second handle by a distance such as to just nicely receive a portion of said first handle therebetween, said second handle and said second handle cover having opposed corresponding mirror image grooves formed therein, said grooves being L-shaped having corresponding first and second legs, said pusher having a rearward end terrminating in a cylindrical lug extending transversely of said pusher through said slot of said first handle and with its ends located in said second handle and second handle cover grooves, respectively, said first groove legs being so configured as to cooperate with said slot and said pusher lug ends to shift said pusher to its retracted position when said handles travel about the first quarter of the distance from their open to their closed positions and to shift said pusher to its extended position when said handles travel about the last quarter of the distance from their closed to their open positions, said second groove legs bering so configured as to cooperate with said slot and said pusher lug to maintain said pusher in said retracted position when said handles travel about the last three quarters of the distance from their open to their closed positions and the first three quarters of the distance from their closed to their open positons.

7. The instrument claimed in claim 6 wherein said second handle has a lug near its forward end, said second jaw having a cam surface thereon, said second handle lug and said second jaw cam surface being so positioned and configured that as said first and second handles are shifted from their open to their closed positions said second handle lug will contact said second jaw cam surface to shift said second jaw to its closed position after said pusher has been shifted to its retracted positon and when said first and second handles are shifted from their closed to their open position said lug will release said cam surface to permit said second jaw to shift to its open position before said pusher is shifted to its extended position.

8. The instrument claimed in claim 7 wherein said magazine comprises an elongated tubular member of C-shaped cross section, said clips being slidably mounted within said tubular member, each of said clips having a crown portion terminating in legs, said clips lying leg-foremost one behind the other in the same plane within said tubular member.

9. The instrument claimed in claim 8 including a pin on said first jaw extending toward said second jaw, said second jaw having a perforation, said pin having a free end located within said second jaw perforation when said jaws are in their open positions, said pin being received within said second jaw perforation when said jaws are in their closed positions, each of said clips having a crown portion terminating in legs, said pin being so located on said first jaw as to be adjacent the crown portion of a clip in clamping position between said jaws to prevent rearward movement of said clip as it is being located about a blood vessel to be clamped.

10. The instrument claimed in claim 9 including extensions of the free ends of said first groove legs, said groove extensions being parallel to said first handle slot when said first and second handles are in their open positions, said pusher lug ends entering said groove extensions upon shifting of said handles from their closed to their open positions after the clamping of the last of said clips to lock said handles in their open positions.

11. The instrument claimed in claim 1 including spring means biasing said handles to their open positions.

12. The instrument claimed in claim 1 including spring means to bias said second jaw to its open position.

13. The instrument claimed in claim 1 including a rectilinear slot in said first handle located rearwardly of said pusher track and extending parallel thereto, said first handle having a cover enclosing said pusher track and exposing said slot, said second handle having a cover affixed thereto in parallel spaced relationship, said second handle cover being spaced from said second handle by a distance such as to just nicely receive a portion of said first handle therebetween, said second handle and said second handle cover having opposed corresponding mirror image grooves formed therein, said grooves being L-shaped having corresponding first and second legs, said pusher having a rearward end terminating in a cylindrical lug extending transversely of said pusher through said slot of said first handle and with its ends located in said second handle and second handle cover grooves, respectively, said first groove legs being so configured as to cooperate with said slot and said pusher lug ends to shift said pusher to its retracted position when said handles travel about the first 25 percent of the distance from their open to their closed positions and to shift said pusher to its extended position when said handles travel about the last 25 percent of the distance from their closed to their open positions, said second groove legs being so configured as to cooperate with said slot and said pusher lug to maintain said pusher in said retracted position when said handles travel about the last 75 percent of the distance from their open to their closed positions and the first 75 percent of the distance from their closed to their open positions.

14. The instrument claimed in claim 13 including extensions of the free ends of said first groove legs, said groove extensions being parallel to said first handle slot when said first and second handles are in their open positions, said pusher lug ends entering said groove extensions upon shifting of said handles from their closed to their open positions after the clamping of the last of said clips to lock said handles in their open positions.

15. The instrument claimed in claim 1 wherein said second handle has a lug near its forward end, said second jaw having a cam surface thereon, said second handle lug and said second jaw cam surface being so positioned and configured that as said first and second handles are shifted from their open to their closed positions said second handle lug will contact said second jaw cam surface to shift said second jaw to its closed position after said pusher has been shifted to its retracted position and when said first and second handles are shifted from their closed to their open positions said lug will release said cam surface to permit said second jaw to shift to its open position before said pusher is shifted to its extended position.

16. The instrument claimed in claim 1 wherein said magazine comprises an elongated tubular member of C-shaped cross section, said clips being slidably mounted within said tubular member, each of said clips having a crown portion terminating in legs, said clips lying leg-foremost one behind the other in the same plane within said tubular member.

17. The instrument claimed in claim 16 wherein said means to constantly urge said row of clips toward the forward end of said magazine comprises a feeder shoe slidably mounted within said tubular member behind said row of clips therein and a constant-force spring engaging said shoe and constantly urging said shoe and said clips toward the forward end of said tubular member.

18. The instrument claimed in claim 1 including a pin said first jaw extending toward said second jaw, said second jaw having a perforation, said pin having a free end located within said second jaw perforation when said jaws are in their open positions, said pin being received within said second jaw perforation when said jaws are in their closed positions, each of said clips having a crown portion terminating in legs, said pin being so located on said first jaw as to be adjacent the crown portion of a clip in clamping position between said jaws to prevent rearward movement of said clip as it is being located about a blood vessel to be clamped.

19. The instrument claimed in claim 1 including means to lock said handles in their open positions after the last of said clips has been clamped.

20. The instrument claimed in claim 1 wherein said ligator is a single-use disposable instrument.

21. An instrument for applying clamping clips to blood vessels, said instrument comprising a first handle terminating at its forward end in a first jaw, a second handle and a second jaw both coupled to said first handle, said first and second handles being manually shiftable between open and closed positions, said first jaw being shiftable by said first handle and said second jaw being shiftable by said second handle between open and closed clip-clamping positions, an elongated magazine coupled to said first handle, a row of clips located within said magazine, clip feed means mounted within a clip feet track, said clip feet track parallel to and adjacent to said magazine and extending to the forward ends of said first and second jaws, said clip feed means being shiftable by said first and second handles between a retracted position removed from said jaws when said handles are in their closed positions and an extended clip-locating position between said jaws when said handles are in their open positions, passage means connecting said magazine and said clip feed track, and means for transferring each clip from the forward end of said magazine to said clip feed track via said passage means, wherein said transfer means is obstructed when said clip feed means is in its extended position, and is enabled when said clip feed means is in its retracted position to cause the forwardmost clip of said row to be transferred from said magazine to said clip feed track.

22. The instrument claimed in claim 21 including spring means biasing said handles to their open positions.

23. The instrument claimed in claim 21 including spring means to bias said second jaw to its open position.

24. The instrument claimed in claim 21 wherein said magazine comprises an elongated tubular member, said clips being slidably mounted within said tubular member, each of said clips having a crown portion terminating in legs, said clips lying leg-foremost one behind the other in the same plane within said tubular member.

25. The instrument claimed in claim 21 wherein said ligator is a single-use disposable instrument.

26. The instrument claimed in claim 21 wherein said clip feed means is substantially removed from said jaws when said first and second handles have travelled at least one quarter of the distance from their open to their closed positions.

27. The instrument claimed in claim 21 wherein said passage means is enabled before said first and second handles have travelled completely to their closed positions.

28. The instrument claimed in claim 21 wherein said transfer means comprises ramping means having at least one surface sloping forwardly at an angle to said clip feed track.

29. The instrument claimed in claim 28 wherein said ramping means further comprises at least one first ramp surface sloping forwardly and toward said clip feed track at a shallow angle and terminating in at least one second ramp surface sloping forwardly and toward said clip feed track at a steeper angle terminating at said clip feed track, said first and second ramp surfaces for one clip leg being spaced apart by a separating portion.

30. The instrument of claim 29, wherein said separating portion comprises a wall portion, said wall portion having a rearward end adjacent the forward end of said magazine, said wall portion rearward end terminating in at least one ramp surface extending forwardly and to said clip feed track to lift the crown of each clip into said clip feed track.

* * * * *